United States Patent [19]

Ariga

[11] Patent Number: 5,364,761
[45] Date of Patent: Nov. 15, 1994

[54] METHOD FOR ISOLATING A DNA ENCODING AN AUTONOMOUSLY REPLICATING SEQUENCE

[75] Inventor: Hiroyoshi Ariga, Tokyo, Japan

[73] Assignee: Daiichi Pharmaceutical Co., Ltd., Tokyo, Japan

[21] Appl. No.: 972,089

[22] Filed: Nov. 5, 1992

Related U.S. Application Data

[63] Continuation of Ser. No. 545,675, Jun. 29, 1990, abandoned, which is a continuation of Ser. No. 77,467, Jul. 24, 1987, abandoned.

[30] Foreign Application Priority Data

Jul. 24, 1986 [JP] Japan .................. 61-174036
Sep. 26, 1986 [JP] Japan .................. 61-227455

[51] Int. Cl.⁵ .................. C12Q 1/68; C12N 5/10; C12N 15/11; C12N 15/88
[52] U.S. Cl. .................. 435/6; 435/7.8; 435/69.1; 435/172.1; 435/172.3; 435/240.2; 435/320.1; 536/23.1; 935/70; 935/77
[58] Field of Search .................. 435/6, 7.8, 69.1, 172.1, 435/172.3, 240.2, 320.1; 935/6, 8, 22, 24, 33, 34, 59, 60, 70, 77; 536/23.1

[56] References Cited

FOREIGN PATENT DOCUMENTS

0045573 10/1982 European Pat. Off. .
0240373 7/1987 European Pat. Off. .

OTHER PUBLICATIONS

Ariga et al., *Molecular and Cellular Biology*, 7:1-6 (1987).
Hsu et al., *Chemical Abstracts*, 99:33863f (1983).
Iguchi-Ariga et al., *EMBO Journal*, 6:2365-2371 (1987).
Montrel et al., Nucleic Acids Research, 12 (1984), pp. 1049-1068.
Perrson et al., Science 225 (1984) 718-720.
Roth et al., Mol. and Cell. Biol. 3 (1983) 1898-1908.
Ariga el al., Mol. and Cell Biol. 5 (1985) 563-568.
Ariga, Mol. Cell Biol. 4:1476-82 (1984), Abstract only.
Falaschi et al., 1985, Chemical Abstracts, vol. 102; Abstract No. 161465v.

*Primary Examiner*—Richard A. Schwartz
*Assistant Examiner*—J. Leguyader
*Attorney, Agent, or Firm*—Sughrue, Mion, Zinn, Macpeak & Seas

[57] ABSTRACT

A plasmid which contains a mammalian cell-derived autonomously replicating sequence DNA, a promoter and a gene for peptide production inclusive of the translation initiation codon.

6 Claims, 4 Drawing Sheets

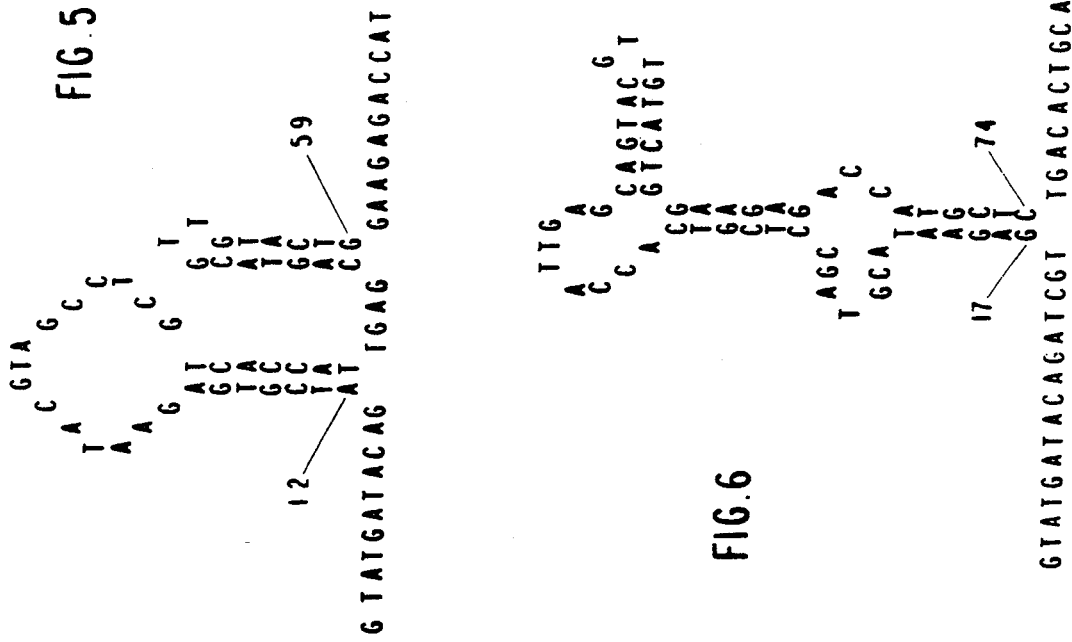
FIG. 5
FIG. 6
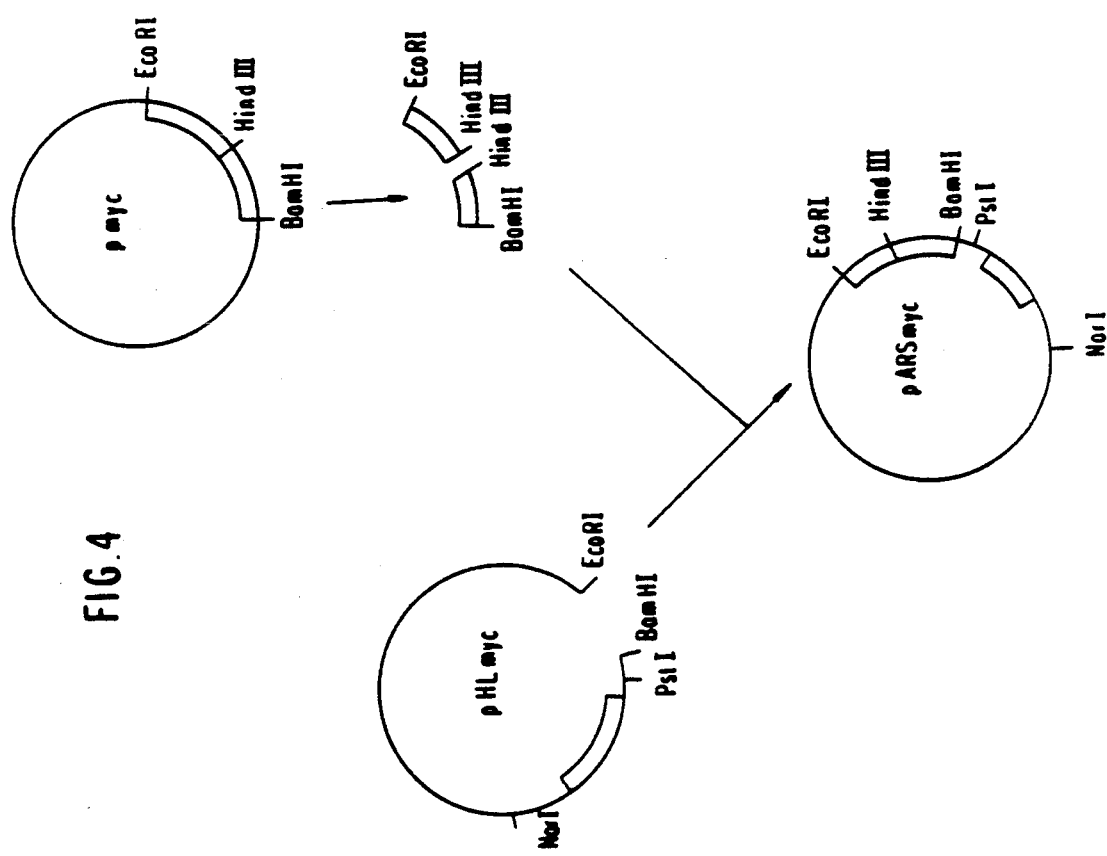
FIG. 4

```
            T C                              T T A
         C     C                          C     T
        T       A                        T       G
       G         T                      C         G
      G           A                    T           C
     86-C:G-99                        A             G
        C:G                       136-C:G-150
        A:T                          A:T
        T G                          C:G
        T:A                          T:A
        A:T                          T:A
 70        80-C:G-105       120       A:T
 TT TCACGTTGC    TTCAT TAGCAGTTGG ATGATAGGT 130-T:A-156
                    110                     GTCA CCTCTT
                                                160
                                           ⇅
```

FIG.7

```
                                    C T T
                                   T     G
                                  C       A
                                 C         A
                                A           C
                                 C         C
                            158-T:A-172
                               G:C
                               A:T
                               T T
                               A:T
             140           153-A:T-177
             TCT CTTATGGCG G TG    TCCT CCAG
                          150        180
```

FIG.8

```
              37                                    66
pHLmyc    5' CCATTGAGCAGTACGTTGTACTGGAAGAGA 3'
              ** *     *    **  *   *** **
pmyc(H-P) 5' TTATTCACATCTCTTATGGCGGTGAATAG  3'
             129                              158

1750                                  1779
pARS65    5' ATGATAACTCTTATATTGGTGTTCAATAAT 3'
              *  ** *    *  *** *  * **** *
pmyc(H-P) 5' TTATTCACATCTCTTATGGCGGTGAATAGT 3'
             129                              158
```

METHOD FOR ISOLATING A DNA ENCODING AN AUTONOMOUSLY REPLICATING SEQUENCE

This is a continuation of application Ser. No. 07/545,675 filed Jun. 29, 1990, now abandoned, which is a continuation of application Ser. No. 07/077,467 filed Jul. 24, 1987, now abandoned.

FIELD OF THE INVENTION

This invention relates to plasmids, to a method of producing peptides, and to a method of recovering mammalian cell-derived autonomously replicating sequence DNAs.

BACKGROUND OF THE INVENTION

Known methods of producing peptides by utilizing genetic engineering techniques include, among others, causing microorganisms such as *Escherichia coli* and *Bacillus subtilis* to produce peptides, proteins and the like by utilizing plasmids and causing hosts to viruses to produce peptides, proteins and the like by utilizing viral DNA.

However, these known methods are not entirely satisfactory with respect to the stability of plasmids, the variety of usable cell species, and production efficiency.

The present inventor previously succeeded in isolating a mouse cell-derived DNA fragment containing an autonomously replicating sequence (ARS) and reported that this fragment is an EcoRI-BglII fragment of about 2,500 base pairs (*Mol. Cell. Biol.*, 5, 563–568 (1985)).

The present inventors carried out further investigations into the properties of this ARS fragment and found that the ARS has affinity for the c-myc protein which is the product of the c-myc gene and that the c-myc protein binds with c-myc gene itself and controls expression thereof. Furthermore the inventor found that not only myc protein but also various DNA-binding proteins have affinity for the ARS. This finding made it possible to separate and obtain the ARS from various mammalian cells using the myc protein and the like. The inventor further found that useful peptides, proteins or glycoproteins, among others, can be produced efficiently by utilizing such a mammalian cell-derived autonomously replicating sequence (ARS), and have now completed the present invention.

SUMMARY OF THE INVENTION

The invention provides a method of recovering mammalian cell-derived autonomously replicating sequence DNAs which comprises binding a mammalian cell-derived DNA fragment to a DNA-binding protein, separating the binding product and isolating the DNA from the binding product; plasmids which contain a mammalian cell-derived autonomously replicating sequence DNA, a promoter and a gene for peptide production (inclusive of the translation initiation codon); mammalian cells transfected with these plasmids; and a method of producing peptides which comprises utilizing the mammalian cell-derived autonomously replicating sequence DNAs, the plasmids or the transformed cells.

BRIEF DESCRIPTION OF THE DRAWINGS

In the accompanying drawings,

FIGS. 1–4 each shows an outlined construction scheme for the respective plasmid, and FIGS. 5 to 7 each shows possible secondary structure of a certain DNA portion to be referred to later herein.

FIG. 8 shows comparison of the DNA sequences between three plasmids.

DETAILED DESCRIPTION OF THE INVENTION

Figure 1:
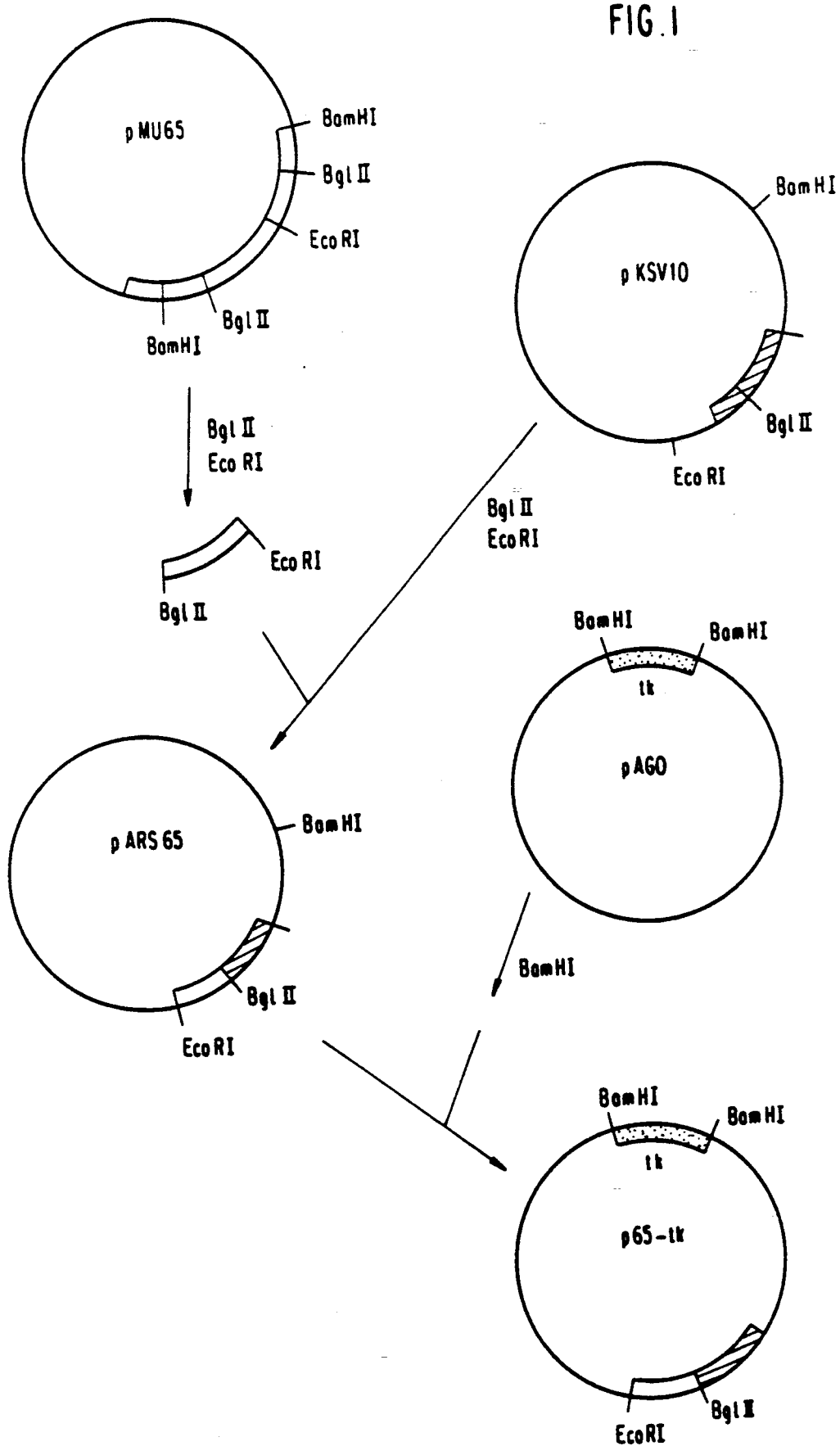

The autonomous replicating sequence or ARS is the origin of replication in autonomous replication eucaryotic chromosomes. The ARS can be obtained in the following manner: DNA is separated from mammalian cells and treated with an appropriate restriction enzyme or enzymes, preferably six-base restriction enzyme such as HindIII, EcoRI, BamHI, etc. The thus-obtained DNA fragments which are normally in the range of 1,000–10,000 base pairs in length are mixed with the DNA-binding protein thereby form a DNA-myc protein complex.

In this specification and claims the DNA-binding protein is defined as the protein that binds with DNA, exists in the mammalian cell nucleus and controls replication or expression of the DNA in the cell, which may be called non-histone protein, and examples of the DNA-binding protein include myc proteins (such as c-myc protein (*Science* 225, 718–720 (1984)), v-myc protein (*Nature* 296, 262–264 (1982)), N-myc protein (*Annu. Rev. Biochem.*, 52, 301–310 (1983)), c-myb protein, v-myb protein, c-fos protein, v-fos protein, p53 (each described in *Annu. Rev. Biochem.* 52 301–310 (1983)), SV40 T antigen (*Cell* 13 165 (1978)) and RB gene product (*Science* 235 1394–1399 (1987)). These proteins may be available in cell nuclear extract as described in the above references, for example, c-myc protein is available in HL-60 cell nuclear extract. For the separation procedure after formation of such DNA-protein complex, conventional means of separation or isolation of proteins, such as the procedure for antigen-antibody reactions or the like may be used.

For example, it is convenient that this complex is further bound to an antibody to the DNA-binding protein and the resultant complex is further bound to a substance capable of specifically binding to the antibody, for example, the second antibody or protein A, to produce a complex having molecular weight as large as forming precipitate. Precipitate of the complex can be collected with ease by a conventional manner such as filtration or centrifugation.

The antibody to the DNA-binding protein can be produced by a general manner such as by immunizing an animal with the protein but it is convenient to obtain from commercial sources such as Oncor Inc., U.S.A. and etc. For example, the third exon of N-myc gene (the specific moiety of N-myc) is expressed in *E. coli* to obtain N-myc protein then a mouse is immuninized with the protein by a general method. Anti-serum is collected from the mouse and the IgG fraction thereof is used as the anti-N-myc protein antibody. (see also *J. Virol.* 34 752–763 (1980)).

The second antibody can also be produced by method known per se, and protein A are provided as a form of cell suspension of *Staphylococcus aureus* (P-7155 (Sigma)) or a combined form with some solid (Protein A-Sepharose CL-4B (Pharmacia) or Protein A-Agarose FPA-1 (Cosmo-Bio Ltd.).

Separation of the DNA from the complex (e.g., DNA=binding protein=antibody=protein A) can be carried out in a conventional manner, for example, by treatment with a reagent such as 2-mercaptoethanol or a proteolytic enzyme (Mol. Cell. Biol. 3, 1958–1966 (1983)) such as Proteinase K (Proteinase K P0390 (Sigma), Proteinase K No. 24568 (Merck)), however, 2-mercaptoethanol is preferable since the proteolytic enzyme may sometimes degradate DNA chain.

It is very important fact discovered by the present inventor that the thus-isolated DNA fragment having specific affinity for the DNA-binding protein contains ARS DNA, and that the DNA-binding protein and ARS have very strong affinity for each other.

The ARS-containing DNA fragment can be utilized either in the form of ARS itself or of an ARS-containing DNA fragment having an appropriate length, as desired.

The size of possible ARS DNA is considered about one hundred base pairs, however, it is also supposed that sometimes the ARS DNA is partially overlapped with an enhancer DNA. So, use can be made of a DNA having several hundreds base pairs as ARS-containing DNA fragment. The techniques of DNA treatment, screening and so on for producing useful substances, for example, peptides, by utilizing the ARS will be apparent and readily understandable to those with ordinary skill in the art when they use conventional or known techniques with reference to the examples given herein and so forth (T. Maniatis et al., *Molecular Cloning*, Cold Spring Harbor Laboratory (1982), hereinafter *Mol. Clon.*).

It is quite possible that the base sequence of the ARS might vary slightly depending on the species of animal used for providing cells from which the ARS is derived, depending on the cell species, or depending on the site which serves as the source of the ARS (when cells of the same strain are used). Therefore, it is not always necessary that an ARS to be used should be completely identical in base sequence to the ARS obtained in the above manner. On the contrary, it is possible to perform partial base substitution in or deletion from or, further, base addition to the ARS. Whether the resulting ARS is suited for efficient production of the desired product can be determined by conventional testing and study with reference to the description given herein.

Referring to the invention, as the isolable or usable ARS, an ARS derived from mammalian cells such as cells of a mouse, rat, guinea pig, cattle, horse, sheep, goat, rabbit, monkey, chimpanzee or human is exemplary. In particular, a mouse or human cell-derived ARS may be considered appropriate since advanced cell culture techniques are available for mouse and human cells.

Though any mammalian cells can be employed as an origin for the production of ARS, it is convenient to use such cells much producing the DNA-binding proteins as c-myc protein as described in *Science* 225, 718–720 (1984), v-myc protein described in *Nature* 296, 262–264 (1982), N-myc protein, c-myb protein, v-myb protein, c-fos protein, v-fos protein, p53 which are described in *Annu. Rev. Biochem.*, 52, 301–310 (1983), SV40 T antigen described in *Cell*, 13, 165 (1978) and RB gene product described in *Science*, 235, 1394–1399 (1987).

Representative examples of such mammalian cells from which ARS is isolated include human HL-60 cell, human IMR-32 cell, human Raji cell, mouse FM3A cell and the like.

The ARS-containing plasmids according to the invention, which are suited for peptide production, can be constructed by utilizing conventional gene recombination techniques (cf. *Mol. Clon.*).

Introduction of the plasmids into cells, selection of the kind of cells to be used, cell proliferation and other necessary procedures can be carried out or made by utilizing those mammalian cell lines or strains and techniques that are generally known in the art. It will be also possible to utilize those techniques, cultured cells, media, and so forth which might be improved or developed in the future. (cf. "*Manual of Cell Culture*", edited by Munemura, Kodansha, Tokyo (1982), K. Habel and N. P. Salzman, *Fundamental Technique in Virology*, Academic Press, N.Y. (1969), Kruse and Patterson, *Tissue Culture*, Academic Press, N.Y. (1973) and *Virology*, 52 456–467 (1973)).

Several examples of the general procedures are given below for further illustration.

Examples of promoters which are usable are cell-derived promoters of various kinds, such as the thymidine kinase promoter and immunoglobulin promoter, and promoters from viruses infectious to mammalian cells, such as the SV40 T antigen promoter or SV40 early promoter, SV40 late promoter, Adenovirus promoters and the herpes virus thymidine kinase promoter. An ordinary ATG can be used as the translation initiation codon.

Examples of peptides to be produced include among others, those peptides, proteins, glycoproteins and the like that are usable as drugs, for example, insulin, growth hormone, interferons, tumor necrosis factor, interleukins, other lymphokines, and various enzymes.

Examples of genes for peptide production include among others, DNAs coding for respective amino acid sequences of the above-mentioned peptides, and sequences composed of the DNAs and a poly(A) signal for terminating translation as added thereto on the 3' downstream side.

The plasmids according to the invention are produced by joining a DNA fragment having an appropriate number of base pairs and one or more sites cleavable with restriction enzymes in common use, a promoter, the translation initiation codon and a gene for peptide production in an appropriate, desired order, further adding an ARS and circularizing the construct.

The direction or location of the ARS need not be considered as particularly limited.

The plasmids thus obtained are introduced into various mammalian cells e.g., by transfection method using calcium phosphate, the microinjection method, the liposome method, the protoplast fusion method or the like, whereby transformed cells can be produced. Mouse NS-1 and FM3A and human HL-60, U937, Daudi and Raji are examples suitable cultured cells but not limited to those. The desired peptides can be produced by growing and multiplying these transformed cells.

A characteristic feature of the invention is that the cells into which the plasmids are to be introduced need not be from the same species as the species from which the ARS is derived. That is, when an ARS DNA is obtained from a mouse cell, the DNA can be used for the expression in another kind of mouse cells and in human cells or in other mammalian cells.

The transformed cells are grown and multiplied by conventional methods of cultivating the cells used, for example, in DMEM (Dulbecco modified Eagle's medium) containing an appropriate amount of fetal calf serum at 37° C. in the presence of 5% carbon dioxide, or in the peritoneal cavity of an animal (cf. "*Manual of Cell Culture*", edited by Munemura, Kodansha, Tokyo (1982), *Fundamental Technique in Virology*, Tissue Culture).

The peptides produced, when they have been released into the medium, can be isolated by conventional fractionation techniques, for example, by centrifugation and/or gel filtration. When the peptides accumulate cells, the peptides can be recovered by ordinary fractionation after disruption of the cells. Also when they are in the ascitic fluid, they can be isolated using conventional techniques.

The following examples are given to further illustrate the present invention but are by no means to be construed to be limitative thereof. Unless otherwise indicated, all parts, percents, ratios and the like are by weight.

EXAMPLE 1

(1) Construction of a Plasmid Containing Mouse ARS and the Thymidine Kinase Gene (cf. FIG. 1)

The plasmid pMU65 (*Mol. Cell. Biol.*, 5 563–568 (1985)) was treated with EcoRI and BglII and a DNA fragment about 2,500 base pairs in length was isolated from this plasmid. This fragment was inserted into the plasmid pKSV10 (commercially available from Pharmacia) in the EcoRI-BglII region thereof, whereby a plasmid, pARS65, was constructed.

The plasmid pAGO (*Proc. Natl. Acad. Sci. USA*, 76, 3755 (1979)) was treated with BamHI and a DNA fragment containing the herpes virus-derived thymidine kinase gene was isolated. This DNA fragment was inserted into the above-mentioned plasmid pARS65 at the BamHI site thereof. The thus-constructed plasmid p65-tk was allowed to multiply in *E. coli* (the transformant containing the plasmid (*E. coli* K12 C600 ARS-1) having been deposited with the Fermentation Research Institute under the deposit number FERM BP-1443).

Figure 2:
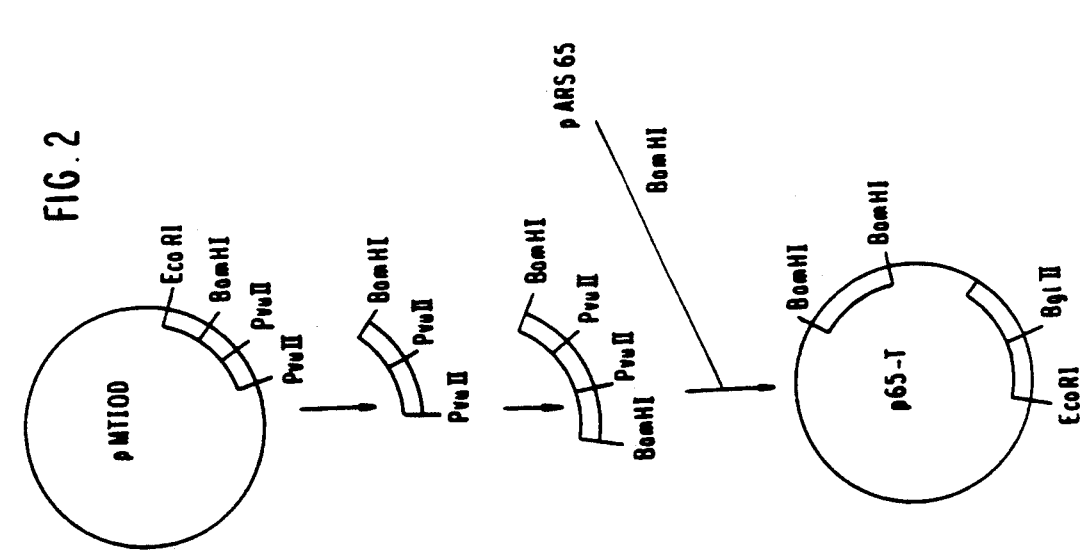

(2) Construction of a Plasmid Containing Mouse ARS and the SV40 T Antigen Gene (cf. FIG. 2)

The plasmid pMTIOD (*J. Virology*, 48, 481–491 (1981)) was treated with BamHI and PvuII and the SV40 T antigen gene with the early promoter therefor was isolated. The BamHI linker (Takara Shuzo, Japan) was joined to the PvuII site of this gene. The fragment thus obtained was inserted into the plasmid pARS65 at the BamHI site thereof to obtain a plasmid, p65-T.

(3) Expression of Protein (thymidine kinase)

The plasmid p65-tk obtained in process (1) above was used to transfect FM3A$^{tk-}$ cells by the liposome fusion method. The plasmid p65-tk was encapsulated in large unilamellar vesicles (LUV$_s$) prepared by the phosphatidyserine calcium induced fusion case. In performing the transformation, 20 mM Tris buffer (pH 7.5) containing 50 mM EDTA was used (cf. *Science* 215, 166 (1982) and *Proc. Natl. Acad. Sci. USA*, 75, 4194 (1978).

After transformation, the cells were grown in DMEM containing 10% fetal calf serum at 37° C. in the presence of 5% carbon dioxide. After 2 days, the medium was replaced with HAT medium.

Transformed cells, namely FM3A$^{tk+}$ cells, were observed in approximately a week. After 2 weeks of cultivation, each colony was isolated and transferred to HAT medium. For each colony, cultivation in HAT medium was continued until the number of cells amounted to about 10$^7$ per colony. The number of doublings during this cultivation period amounted to about 60.

One thousand cells were subjected to transformation by the above method, whereupon about 300–400 transformant cells were obtained. It was thus confirmed that p65-tk had propagated in FM3A$^{tk-}$ cells and the thymidine kinase gene had been expressed.

(4) Checking for Copy Number

The above-mentioned 10$^7$ cells were extracted and obtained low molecular weight DNA fraction by the Hirt method (*J. Mol. Biol.*, 26, 365–369 (1967)). To confirm plasmid replication in the transformants, the low-molecular-weight DNA fraction was treated with the restriction enzyme DpnI.

While p65-tk introduced into FM3A$^{tk-}$ cells contains a methylated adenine moiety, the replication product yielded in these cells did not contain any methylated adenine group. Since DpnI cleaves methylated DNA selectively, it cleaves exclusively the plasmid introduced into the cells to give a plurality of DNA fragments, with the plasmid copies replicated in the cells remaining uncleaved. Therefore, the plasmid copies replicated in the cells can be easily distinguished by electrophoresis.

After DpnI digestion, DNAs were separated by agarose gel electrophoresis (*Mol. Clon.*) and subjected to Southern blot testing (*J. Mol. Biol.*, 98, 503–517 (1975)). Thus, hybridization was carried out using $^{32}$P-labeled p65-tk as a probe, followed by X-ray autoradiography. Detection of bands hybridized to the probe confirmed that p65-tk had been replicated as an extrachromosomal DNA in all of the 20 clones investigated.

The copy number per cell estimated from the band intensity was 100–200. This plasmid was replicable in a stable manner also when the above cells were grown in DMEM containing 10% fetal calf serum, which was used in lieu of HAT medium. No modification was noted in the DNA level. It was also confirmed that this plasmid remained in the cells in a stable manner even after the lapse of the time for 150 doublings.

(5) Replication of Plasmid pARS-65 in Different Cell Lines pARS-65 was transfected into mouse NS-1 cells, human HL-60 cells, and human U937 cells, respectively, using the method described above. The cells were then grown in RPMI 1640 medium containing 10% fetal calf serum at 37° C. in the presence of 5% carbon dioxide. After 40 hours, the extrachromosomal low-molecular-weight DNA was analyzed by the method mentioned above in (4). As a result, about 500 copies of pARS-65 were confirmed to have been replicated in each NS-1 cell, about 10,000 copies were confirmed to have been replicated in each HL-60 cell, and about 100 copies were confirmed to have been replicated in each U937 cell.

It was thus confirmed that pARS-65 is replicable also in cells of other species than mouse. At the same time, the results suggest that p65-tk might have such replicability.

Example 2

Figure 3:
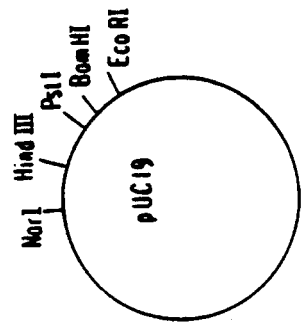
Figure 3:
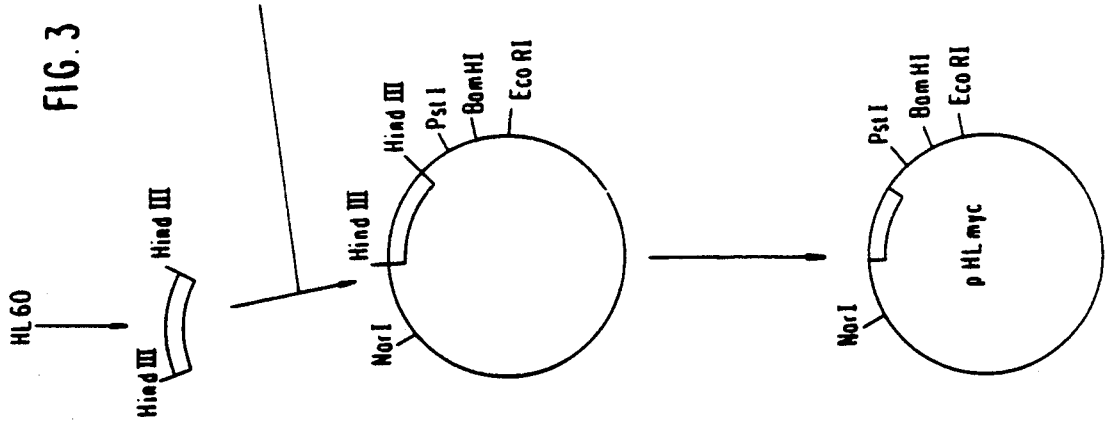

1) Isolation of Human Cell-Derived ARS (cf. FIG. 3)

Human HL-60 cell DNA was extracted using the SDS-proteinase K method (*Mol. Clon.*) and treated with HindIII. A DNA fragment having affinity for the myc protein wax obtained from the DNA fragment mixture thus obtained, using a conventional method (*Mol. Cell. Biol.*, 3, 1958–1966 (1983)) as follows:

The above fragment mixture was mixed with an HL-60 nuclear extract (rich in myc protein), and the reaction was allowed to proceed at 0° C. for 30 minutes, yielding a DNA-myc protein complex.

Then, an anti-myc protein antibody (α-myc, commercially available from Oncor Inc. U.S.A.) was added, whereby a DNA-myc protein-αmyc complex was formed. Furthermore, an aqueous solution of *Staphylococcus aureus*, which contained protein A capable of specifically binding to α myc, was added to form a DNA-myc protein-α myc-protein A complex.

This complex, which occurred as a precipitate, was collected by centrifuging, washed with Tris buffer (pH 7.5) containing 0.1% SDS and 0.1M sodium chloride, and then the DNA was released by adding a 7 mM aqueous mercaptoethanol solution containing 1% SDS and allowing the reaction to proceed at 30° C. for 30 minutes. The reaction mixture was centrifuged at 15,000×g for 5 minutes. The supernatant thus separated was extracted with phenol to remove proteins. The desired DNA fragment thus obtained was inserted into pUC19 (commercially available from Pharmacia) at the HindIII site thereof. The number of base pairs in the above DNA fragment was estimated at about 200 by agarose gel electrophoresis.

The plasmid obtained was multiplied in *E. coli* (the transformant with the plasmid (*E. coli* K12 C600 ARS-2) having been deposited with the Fermentation Research Institute under the deposit number FERM BP-1444).

The above-described HL-60 nuclear extract was prepared in the following manner. Thus, 1 liter of HL-60 cell culture fluid (5×10⁵ cells/ml) was centrifuged and the cells harvested were washed with phosphate-buffered physiological saline. The cells were further washed with a hypotonic aqueous solution (20 mM HEPES, pH 7.5, 5 mM potassium chloride, 0.05 mM magnesium chloride, 0.5 mM dithiothreitol, 0.2 mM sucrose) and then suspended in a hypotonic aqueous solution (the former solution without any sucrose), and the suspension was allowed to stand for 10 minutes. After homogenization by 40 strokes in a Dounce homogenizer, the homogenate was centrifuged at 3,000×g for 10 minutes to obtain a precipitate.

The precipitate comprising cell nuclei was dissolved in 2.5 ml of an aqueous solution (5 mM HEPES, pH 7.5, 10% sucrose) and stored temporarily in liquid nitrogen. After thawing this gradually at 0° C., 5M aqueous sodium chloride was added to a final concentration of 0.1M and, after 5 minutes of treatment at 0° C., the mixture was centrifuged at 15,000×g for 20 minutes to obtain the nuclear extract as a supernatant.

The above-mentioned plasmid as multiplied in *E. coli* K12 C600 was isolated (*Mol. Clon.*). Treatment with HindIII failed to cleave this plasmid. Hence it was considered that bacterial rearrangement of the plasmid had occurred. This plasmid was designated pHLmyc.

The plasmid pUC19 has other restriction enzyme cleavage sites (e.g. BamHI and NarI sites) than the HindIII site. Therefore, the above plasmid was treated with BamHI and NarI, and the smaller, in molecular weight of the two DNA fragments thus formed was isolated.

A $^{32}$P-labeled probe was prepared using this smaller fragment as the template and used for Southern hybridization (*J. Mol. Biol.*, 98, 503–517 (1975)) to the HL-60 cell DNA. This probe hybridized to the HL-60 cell DNA and it was thus confirmed that the fragment having an NarI site at one end and a BamHI site at the other (NarI-BamHI fragment) contained an HL-60 cell-derived DNA.

The length of the NarI-BamHI fragment as estimated by agarose gel electrophoresis was about 200–300 based pairs.

In pUC19, the HindIII site is 131 base pairs apart from the NarI site and 35 base pairs apart from the BamHI site, and a PstI site is present 25 base pairs apart from the BamHI site. In the plasmid pHLmyc, the PstI site was retained. Therefore, the number of base pairs in the HL-60 cell-derived DNA contained in the plasmid pHLmyc was estimated to be about 120.

This base sequence was determined and 99 bases were identified in the HindIII site within the polylinker region. The sequence thereof is shown below:

```
1
GTATGATACAGATCGTGAGAATACGTAGCCTCGTCACCATTGAGCAGTA
CGTTGTACTGGAAGAGACCATGCTCTGACACTGCACGACGTGACAGCATC
                                                99
```

Examination of this sequence for inverted repeats suggested the possibility that it might have hairpin structures as shown in FIG. 5 and FIG. 6. On that basis, it was presumed, of the above 99 bases, bases 12 to 59 or bases 17 to 74 constituted the most important portion of the autonomously replicating sequence (ARS).

(2) Confirmation of Plasmid pHLmyc Containing ARS

HL-60 cells were transfected with pHLmyc by the liposome method, and the copy number was estimated by the method described above and found to be 10,000 per cell.

(3) Construction of Plasmid Containing Human ARS and c-myc and Expression Thereof (cf. FIG. 4)

The plasmid pmyc (commercially available from Oncor Inc. U.S.A.; containing the myc structural gene and the Rous sarcoma virus-derived long terminal repeat promoter (LTR)) was treated with BamHI, HindIII and EcoRI, and the myc structural gene and LTR were isolated and inserted into pHLmyc in the EcoRI-BamHI region thereof. The thus-constructed plasmid pARSmyc was transfected into human U937 cells by the liposome method and the cells were grown in RPMI 1640 medium containing 10% fetal calf serum at 37° C. in the presence of 5% carbon dioxide.

After 3 days of incubation, the quantity of mRNA corresponding to the myc gene as occurring in the cells was determined by the Northern hybridization method (*Mol. Clon.*) and found to be about 100 times greater as compared with the quantity of the mRNA in pARS-free U937 cells. Therefore, it was concluded that mRNA transcription from the myc gene in the plasmid pARSmyc had taken place.

Example 3

(1) Sub-Cloning of Human c-myc Gene

Human c-myc gene (Mol. Cell Biol., 5, 414–418 (1985)) was digested with HindIII and KpnI and the upstream HindIII-KpnI region (about 1,200 bp) was separated. Similarly, the upstream HindIII-PstI fragment was obtained by treating the gene with HindIII and PstI. These fragments were subcloned into pUC18 and pUC19 at the corresponding site, respectively, and the resultant plasmids of the clone were designated pmyc (H-K) and pmyc (H-P), respectively. Plasmid pmyc (H-P) was used to transform a dam+ E. coli to yield transformed strain MV1184, which was deposited at the fermentation Research Institute on Jun. 30, 1988 under accession number FERM-BP 1932, in accordance with the provisions of the Budapest Treaty.

(2) Binding of the HindIII-KpnI Fragment and HindIII-PstI Fragment with c-myc Protein Gel-shift assay method has been recently employed to examine binding of DNA with a protein (Nucleic Acid Res., 9, 3047–3060 (1981)). In the method, an isotope-labelled DNA is treated with a protein to bind and eluted on polyacrylamide gel, so the DNA-protein complex is late to move on the gel.

The nuclear extract of HL-60 cell which was much producing c-myc protein was used as the c-myc protein source. Each HindIII-KpnI fragment and HindIII-PstI fragment described above was mixed with the nuclear extract and warmed at 30° C. for 15 minutes. The resulting mixture was eluted on polyacrylamide gel. On the other hand, the nuclear extract was pre-treated with anti-myc protein antibody (Oncor Inc. U.S.A.), which was then treated in the same manner as above with the above fragments, respectively.

The each fragment was bound with protein, however, pretreated protein with antibody were not bound with the fragment. From the fact it was concluded that there is a binding site with the c-myc protein in the HindIII-PstI fragment (about 200 bp). (3) Plasmid pmyc (H-K) was digested with HindIII and KpnI, whereas pmyc (H-P) was digested with HindIII and PstI to produce DNA fragments. Each fragment was treated similarly to Example 2 with c-myc protein, antibody and protein A in turn and the complexes were treated with 2-mercaptoethanol to cause protein degradation and to remove resulted proteins.

Thus, the HindIII-KpnI fragment and the HindII-PstI fragment were obtained and DNA sequence of the HindIII-PstI fragment was determined by the dideoxy chain termination method, which is shown below.

```
1                                    30
AAGCTTGTTTTGGCCGTTTGTAGGGTTTGT
TGGAATTTTTTTTCCGTCTGTGTACTTCG
TCGAATTATTTCACGTTGCCATTACCGGTT
CTCCATAGGGTGATGTTCATTAGCAGTTGG
ATGATAGGTTATTCACATCTCTTATGGCGG
TGAATAGTCACCTCTTGAACCACTTTTTCC
TCCAGTAACTCCTCTTTCTTCGGACCTTCT
GCAG
```

A possible secondary structue of the sequence was estimated by computor-assisted sequence analysis and is shown in FIG. 7. FIG. 8 shows comparison of the sequence between the fragment of pHLmyc and pmyc (H-P) and between the fragment of pARS65 and pmyc (H-P). Stars indicates matched sequences and sequence with bar is supposed to make stem of hairpin loop. The DNA sequence to make the stem, especially the nine base pairs of GTGAATAGT is considered most important.

Example 4

Similarly to the procedure in Example 2, several plasmids were obtained from various cell nuclear DNA, proteins and antibodies. The name of plasmid and the raw materials were shown in the following table.

| Plasmid | DNA/Enzyme Used | Nuclear Extract of (Protein) | Antibody |
|---|---|---|---|
| pIMR-N | IMR 32 DNA/HindIII | IMR 32 cell (N-myc protein) | anti-N-myc protein |
| pRJ-53 | Raji DNA/HindIII | Raji cell (p53) | anti p53 |
| pHLmyc (Ex. 2) | HL-60 DNA/HindIII | HL-60 cell (c-myc protein) | anti-c-myc protein |

Identification of ARS

Plasmids pmyc (H-K), pmyc (H-P), pIMR-N and pRJ-53 were introduced into cell in a similar manner to Example 1 (3) and the copy number was investigated. The results are shown below.

| Plasmid | Cell | Copy Number |
|---|---|---|
| pmyc (H-K) | HL60 | 1000–5000 |
| pmyc (H-P) | HL60 | 1000–5000 |
| pIMR-N | IMR-32 | 1000–5000 |
| pRJ-53 | Raji | 1000–5000 |

As described in detail hereinabove, the plasmids according to the invention can be replicated with good efficiency in various mammalian cells due to the function of the ARS; the plasmid copy number per cell is high and the gene product production efficiency is high. Therefore, the present invention also provides a peptide production which is excellent from the genetic engineering viewpoint.

While the invention has been described in detail and with reference to specific embodiments thereof, it will be apparent to one skilled in the art that various changes and modifications can be made therein without departing from the spirit and scope thereof.

What is claimed is:

1. A method of recovering a DNA fragment consisting of an autonomously replicating sequence which comprises the steps of:
   (1) binding a mammalian DNA-binding protein selected from the group consisting of N-myc protein, p53 protein and c-myc protein to a human cell-derived DNA fragment having affinity to the DNA-binding protein,
   (2) separating the resulting bound DNA fragment/DNA-binding protein product, and
   (3) isolating the DNA having autonomously replicating activity from said bound DNA fragment/DNA-binding protein product.

2. An isolated autonomously replicating DNA sequence obtained by the process of claim 1.

3. A plasmid which contains an autonomously replicating DNA sequence, a promoter and a gene for peptide production inclusive of the translation initiation codon, wherein said autonomously replicating DNA sequence DNA is obtained by the steps of:

(1) binding a mammalian DNA-binding protein selected from the group consisting of N-myc protein, p53 protein and c-myc protein to a human cell-derived DNA fragment having affinity to the DNA-binding protein, (2) separating the resulting bound DNA fragment/DNA-binding protein product, and (3) isolating the DNA having autonomously replicating activity from said bound DNA fragment/DNA-binding protein product.

4. A mammalian cell in culture, other than a T-antigen producing cell, transfected with a plasmid containing an autonomously replicating DNA sequence, a promoter and a gene for peptide production inclusive of the translation initiation codon, wherein said autonomously replicating DNA sequence DNA is obtained by the steps of:

(1) binding a mammalian DNA-binding protein selected from the group consisting of N-myc protein, p53 protein and c-myc protein to a human cell-derived DNA fragment having affinity to the DNA-binding protein, (2) separating the resulting bound DNA fragment/DNA-binding protein product, and (3) isolating the DNA having autonomously replicating activity from said bound DNA fragment/DNA-binding protein product.

5. An autonomously replicating sequence obtained from the 5' non-coding region of the human c-myc gene by digestion with Hind III and Pst I.

6. Plasmid pmyc (H-P) or the autonomously replicating sequence therefrom.

* * * * *